United States Patent
Krueger et al.

(10) Patent No.: US 12,251,189 B2
(45) Date of Patent: Mar. 18, 2025

(54) POSITION FEED BACK INDICATOR FOR MEDICAL IMAGING

(71) Applicant: KONINKLIJKE PHILIPS N.V., Eindhoven (NL)

(72) Inventors: Sascha Krueger, Hamburg (DE); Christian Stehning, Hamburg (DE); Peter Mazurkewitz, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 750 days.

(21) Appl. No.: 16/972,636

(22) PCT Filed: Jun. 4, 2019

(86) PCT No.: PCT/EP2019/064404
§ 371 (c)(1),
(2) Date: Dec. 7, 2020

(87) PCT Pub. No.: WO2019/238462
PCT Pub. Date: Dec. 19, 2019

(65) Prior Publication Data
US 2021/0244283 A1 Aug. 12, 2021

(30) Foreign Application Priority Data
Jun. 11, 2018 (EP) .................................... 18176909

(51) Int. Cl.
*A61B 5/00* (2006.01)
*A61B 5/055* (2006.01)
(Continued)

(52) U.S. Cl.
CPC .......... *A61B 5/0036* (2018.08); *A61B 5/0077* (2013.01); *A61B 5/055* (2013.01);
(Continued)

(58) Field of Classification Search
CPC ..... A61B 5/0036; A61B 5/0077; A61B 5/055; A61B 5/704; A61B 5/7221; A61B 5/744;
(Continued)

(56) References Cited

U.S. PATENT DOCUMENTS

| | | | |
|---|---|---|---|
| 6,937,696 B1 * | 8/2005 | Mostafavi | A61B 5/055 378/65 |
| 10,282,064 B2 | 5/2019 | Vahala et al. | |
| 2005/0054910 A1 | 3/2005 | Tremblay et al. | |
| 2005/0283068 A1 | 12/2005 | Zuccolotto et al. | |

(Continued)

FOREIGN PATENT DOCUMENTS

| | | |
|---|---|---|
| JP | 20130146343 A | 8/2013 |
| JP | 2016083417 A | 5/2016 |

OTHER PUBLICATIONS

Wezel et al., "Automated eye blink detection and correction method for clinical MR eye imaging", J Mag. Res. Med., 78, pp. 165-171, 2017.
(Continued)

*Primary Examiner* — Sean A Frith

(57) ABSTRACT

The invention provides for a medical instrument (100, 300, 400, 500, 600) comprising a camera system (102, 102', 102") for imaging a portion (418) of a subject (108) reposing on a subject support (106). The medical instrument further comprises a display system (104) for rendering a position feedback indicator (130, 900). The display system is configured such that the position feedback indicator is visible to the subject when the subject is reposing on the subject support. The execution of the machine executable instructions (120) causes a processor (114) controlling the medical instrument to: acquire (200) a base position image (122) using the camera system; repeatedly (202) acquire a subsequent image (124) using the camera system; repeatedly (204) calculate an image transformation (126) from voxels of at least a portion of the base position image to voxels of the subsequent image by inputting the base position image
(Continued)

and the subsequent image into an image transformation algorithm (128); and repeatedly (206) render a position feedback indicator (130, 900) on the display, wherein the position feedback indicator is controlled by the image transformation.

17 Claims, 10 Drawing Sheets

(51) Int. Cl.
    *A61N 5/10*         (2006.01)
    *G01R 33/28*       (2006.01)
    *G01R 33/385*      (2006.01)
    *G01R 33/565*      (2006.01)

(52) U.S. Cl.
    CPC ............ *A61B 5/704* (2013.01); *A61B 5/7221* (2013.01); *A61B 5/744* (2013.01); *A61N 5/1048* (2013.01); *G01R 33/283* (2013.01); *G01R 33/385* (2013.01); *G01R 33/56509* (2013.01)

(58) Field of Classification Search
    CPC .. A61N 5/1048; G01R 33/283; G01R 33/385; G01R 33/56509
    See application file for complete search history.

(56) References Cited

U.S. PATENT DOCUMENTS

| | | | |
|---|---|---|---|
| 2012/0051664 A1* | 3/2012 | Gopalakrishnan | G06T 5/40 382/294 |
| 2014/0205140 A1 | 7/2014 | Lovberg et al. | |
| 2014/0275962 A1* | 9/2014 | Foo | A61B 5/113 600/411 |
| 2014/0378816 A1 | 12/2014 | Oh et al. | |
| 2015/0196780 A1 | 7/2015 | Tijs et al. | |
| 2015/0208981 A1* | 7/2015 | Oh | G01R 33/48 600/411 |
| 2015/0265220 A1 | 9/2015 | Ernst et al. | |
| 2016/0022240 A1* | 1/2016 | Yamagata | A61B 6/5235 382/131 |
| 2016/0328852 A1* | 11/2016 | Beall | G06N 7/01 |
| 2016/0331239 A1 | 11/2016 | Maclaren et al. | |
| 2017/0281041 A1 | 10/2017 | Yokosawa et al. | |
| 2017/0319143 A1* | 11/2017 | Yu | A61B 5/682 |

OTHER PUBLICATIONS

International Search Report and Written Opinion from PCT/EP2019/064404 mailed Jul. 29, 2019.
Deanna J. Greene et al: "Behavioral interventions for reducing head motion during MRI scans in children", NeuroImage,vol. 171, May 1, 2018 (May 1, 2018), pp. 234-245, X P055521000,Amsterdam, NL ISSN: 1053-8119, DOI:10.1016/j.neuroimage.2018.01.023 p. 234-p. 238.

* cited by examiner

POSITION FEED BACK INDICATOR FOR MEDICAL IMAGING

CROSS REFERENCE TO RELATED APPLICATIONS

This application is a U.S. national phase application of International Application No. PCT/EP2019/064404 filed on Jun. 4, 2019, which claims the benefit of EP application Ser. No. 18/176,909.2 filed Jun. 11, 2018 and is incorporated herein by reference.

FIELD OF THE INVENTION

The invention relates to medical imaging, in particular to the positioning of subjects during medical imaging.

BACKGROUND OF THE INVENTION

Various medical imaging modalities such as computer tomography (CT), magnetic resonance imaging (MRI), positron emission tomography (PET), and others can be used for imaging the internal anatomy of a subject. For example, a large static magnetic field is used by Magnetic Resonance Imaging (MRI) scanners to align the nuclear spins of atoms as part of the procedure for producing images within the body of a subject. This large static magnetic field is referred to as the B0 field or the main magnetic field. Various quantities or properties of the subject can be measured spatially using MRI. However, the acquisition of a magnetic resonance imaging data and other types of medical imaging data is not instantaneous. The subject may need to remain as motionless as possible for a number of minutes.

United States patent application US 2005/0283068 discloses an MRI Digital Video Projection System is which provides a display to the patient to better inform, instruct, test, and comfort the patient plus the potential to stimulate the brain with microsecond onset times to better diagnose brain function. An MRI Motion Tracker and Patient Augmented Visual Feedback System enables monitoring patient body part motion, providing real time feedback to the patient and/or technician to substantially improve diagnostic yield of scanning sessions, particularly for children and mentally challenged individuals. An MR Forward Predictive Noise Canceling Microphone System removes the intense MRI acoustic noise improving patient communication, patient safety and enabling coding of speech output. These systems can be used individually but maximum benefit is from providing all three.

SUMMARY OF THE INVENTION

The invention provides for a medical instrument, a computer program product, and a method in the independent claims. Embodiments are given in the dependent claims.

During the acquisition of medical imaging data or magnetic resonance imaging data it may be difficult for a subject to remain still the whole time or to return to the subject's original position once the subject has moved. This may lead to a degradation of the resulting medical image or cause artifacts in the image. Embodiments may provide a means for a subject to regulate or control the subject's position themselves. A camera system is used to image a portion of the subject. A base image is acquired and then subsequent images are repeatedly acquired by the camera system. An image transformation algorithm is then used to calculate an image transformation between at least a portion of the base position image and each of the subsequent images.

The image transformation algorithm may take different forms in different examples. In one example the image transformation algorithm maps the displacement of a voxel to a different position in a second image. For example, the displacement of voxels in the base position image to a location in a subsequent image. This sort of image transformation algorithm is a displacement mapping algorithm or an optical flow algorithm.

In other examples, the transformation algorithm may also or alternatively map an intensity transformation between at least a portion of the base position image and each of the subsequent images. The resulting image transformation may then be a mapping of voxel intensities to a new voxel intensity. In some case the resulting image transformation is a gradient of the mapping of the voxel intensities to the new voxel intensities.

The term voxel is used throughout this application, but in case of the use of a two-dimensional camera system the voxel is practically reduced to a pixel. Because of this, the term voxel, as used in the context of the presently claimed invention, specifically and explicitly also includes a two-dimensional form thereof, i.e. a pixel.

A position feedback indicator that is controlled by the image transformation can be presented to the subject using a display. This may provide a simple and effective means for the subject to self-regulate their movement and position.

In one aspect the invention provides for a medical instrument comprising a camera system that is configured for imaging a portion of the subject reposing on a subject support. The subject may for example be placed sitting on or leaning on the subject support.

The medical instrument further comprises a display system for rendering a position feedback indicator. The display system is configured such that the position feedback indicator is visible to the subject when the subject is reposing on the subject support. The medical instrument further comprises a memory for storing machine-executable instructions. The medical instrument further comprises a processor for controlling the medical instrument. Execution of the machine-executable instructions causes the processor to acquire a base position image using the camera system. Execution of the machine-executable instructions further causes the processor to repeatedly acquire a subsequent image using the camera system.

Execution of the machine-executable instructions further causes the processor to repeatedly calculate a image transformation from voxels of at least a portion of the base position image to voxels of the subsequent image by inputting the base position image and subsequent image into an image transformation algorithm. The image transformation algorithm is configured for mapping the position of a voxel in the subsequent image. Execution of the machine-executable instructions further causes the processor to repeatedly render a position feedback indicator on the display. The position feedback indicator is controlled by the image transformation. This embodiment may be beneficial because it may provide a means for the subject to either maintain a particular position and/or to return to the position the subject was in when the base position image was acquired.

The camera system could be configured in different ways. In one example the camera system could be a two-dimensional camera system. In other examples the camera system could include a three-dimensional camera system. In other examples there may be multiple cameras that are used for acquiring the base position image.

The image transformation algorithm could in one example be an optical flow mapping algorithm. In this case, the image transformation could a vector mapping.

The image transformation algorithm could in another example be an intensity change detection algorithm. In this case, the image transformation could be scaling factors which rescale the intensity of each voxel. It may be possible to derive an alternative vector mapping from the scaling factors by taking their gradient.

In an example the image transformation algorithm could be any one of the following: an optical flow algorithm, a phase correlation algorithm, a block-based method that minimizes a sum of squared differences or sum of absolute differences or maximizing normalized cross-correlation; and a differential method of estimating optical flow, based on partial derivatives of the image signal and/or the sought flow field and higher-order partial derivatives. The differential methods could include: a Lucas-Kanade method, a Horn-Schunck method, a Buxton-Buxton method, and a Black-Jepson method.

Embodiments may also provide a means for a subject in performing various tasks during a medical imaging or treatment routine. For example, the position feedback may assist a subject in holding his or her breath at a proper time or for a proper duration.

In another embodiment execution of the machine-executable instructions further causes the processor to calculate an average transformation quantity for voxels within a region of interest of the base position using the image transformation. For example, the image transformation could be an average of the vector mapping produced by an optical flow algorithm. This may result in an average vector displacement. The position feedback indicator is controlled using the average transformation quantity. In this embodiment a region of interest of the base position image may be selected.

If the image transformation is the vector mapping, the vectors that are determined for this region may then be used to calculate an average vector displacement. For example, the value of all of the vectors within the region of interest could be summed and then divided by the number of vectors obtaining an average vector displacement. A weighting factor for vectors within different positions within the region of interest may also be used. The use of the average vector displacement to control the position feedback indicator may be beneficial because it may provide for an easy and straight forward means of controlling the position feedback indicator by a subject. For example, the subject may be untrained or unfamiliar with the use of the position feedback indicator. The use of the average vector displacement may be useful for representing different types of motion and require a minimal amount of training for the subject to use properly.

The average transformation quantity could in some examples be used to replace a joystick control. This may enable the use of other software or programs which may display an object which can be controlled or positioned on the position feedback indicator. The average vector displacement mentioned above, could for example easily be used to replace a joystick control.

In another embodiment the position feedback indicator shows a displacement of an object relative to an initial position of that object. For example, the displacement could be directly controlled or related to the average transformation quantity such as the average vector displacement.

In another embodiment the position feedback indicator shows a displacement of a ball relative to a circle. This for example may be a very simple control which a subject can use with a minimal amount of training. As the subject gradually adjusts his or her position the displacement of the ball will go nearer to the circle.

In another embodiment the position feedback indicator shows a displacement of an animated person relative to an initial position of that animated person. For example, the region of interest may be selected for a particular portion of the subject anatomy. For example, the region of interest may be for the face, thorax or even a limb or other body part. The position of this body part could then be indicated within the animation.

In another embodiment the position feedback indicator is a rendering of the image transformation. For example, the base position image could be displayed with a rendering of the image transformation superimposed on this. This may be useful because the subject may be able to see which portion of the subject is in the wrong place by looking at the image transformation.

This could for example be displayed in a variety of different ways. In one example it could be a plot showing a vector for each of the voxel or the voxels if the image transformation is the vector mapping. In other examples, the image transformation could also be rendered using a false color plot. In both cases, rendering of the image transformation could for example be displayed upon the base position image so that the subject knows what part is out of position.

In another embodiment the medical instrument further comprises a medical imaging system configured for acquiring medical imaging data from a subject. The camera system is configured for imaging the portion of the subject when the medical imaging system is acquiring the medical imaging data. This for example may be beneficial because in some medical imaging techniques it may take several minutes to acquire the data for constructing an image. The use of the position feedback indicator may assist the subject in remaining still during the acquisition of the medical imaging data.

In another embodiment the medical imaging system is configured for acquiring the medical imaging data in portions. Execution of the machine-executable instructions further causes the processor to calculate statistical measures from the image transformation. Execution of the machine-executable instructions further cause the processor to retrospectively validate or invalidate the portions of the medical imaging data by comparing the statistical measure to the predetermined criteria. This embodiment may be beneficial because the image transformation is used to retrospectively validate the acquisition of the medical imaging data as it is acquired. This may enable such things as re-acquisition of the data or an exclusion of data which is corrupted by motion of the subject.

The statistical measure of the image transformation could take different forms in different examples. For example, the degree of motion such as a maximum displacement, an average displacement or a maximum displacement within a certain size of neighborhood of voxels may be used to trigger the validation or invalidation of the portions of the medical imaging data.

In another embodiment the medical imaging system is configured for acquiring the medical imaging data in portions. Execution of the machine-executable instructions further cause the processor to calculate a frame-to-frame image transformation by inputting sequentially acquired images selected from the repeatedly acquire subsequent images into the optical flow mapping algorithm. Execution of the machine-executable instructions further cause the processor to calculate a statistical measure from the frame-to-frame image transformation.

Execution of the machine-executable instructions further causes the processor to retrospectively validate or invalidate the portions of the medical imaging data by comparing the statistical measure to a predetermined criteria. In this embodiment the change from frame-to-frame is compared using the statistical measure and then is used to perform the retrospective validation or invalidation. Changes which have been made in the subject since the base position image can be used to identify or validate data. For example, this may be useful in identifying motions which are involuntary and take place on a short timescale. For example, an eye blink or other involuntary motion may create a difference between several images and those which were acquired previously or after that particular image.

For example, comparing the particular image to the base position image may be useful in identifying gross motion of the subject and/or voluntary motion of the subject. The calculation of the statistical measure between the frame-to-frame image transformation may be more useful in identifying motions which the subject is not able to control.

In another embodiment execution of the machine-executable instructions further cause the processor to reacquire invalidated portions of the medical imaging data.

In another embodiment execution of the machine-executable instructions further causes the processor to reconstruct a medical image from the medical imaging data. The reconstruction may exclude invalidated portions of the medical imaging data. This may be beneficial because it may remove data that may wind up corrupting the medical image. This for example may be useful in monitoring the position retrospectively to identify transient motion like eye blinking, swallowing, coughing and also the pulse or beat of a subject's heart.

In another embodiment execution of the machine-executable instructions further causes the processor to calculate the statistical measure. Execution of the machine-executable instructions further causes the processor to calculate a statistical variation of the repeatedly calculated statistical measure. Execution of the machine-executable instructions further causes the processor to adjust the predetermined criteria using the statistical variation. In this embodiment as the subject is continually imaged the predetermined criteria for labeling portions of the medical imaging data as valid or invalid is shifted. For example, some subjects may be better at remaining still than other subjects. In this case the predetermined criteria can be adjusted such that a particular state of motion by that particular subject can be maintained. As a concrete example an adult who is in good health may have an easier time of staying still than a child. In this case the predetermined criteria can be automatically adjusted so that data from the adult is held to a higher standard when it is labeled as being valid or invalid. Likewise, because the child is unable to stay still if the predetermined criteria were too stringent then it would not be possible to complete the imaging protocol.

In another embodiment the medical imaging system is a magnetic resonance imaging system.

In another embodiment the camera system comprises any one of the following: one or more magnet bore mounted cameras, a head coil mounted magnet, one or more magnetic flange mounted cameras, and combinations thereof.

In another embodiment the medical instrument further comprises a second medical imaging system configured for acquired second medical imaging data from the subject. The camera system is configured for imaging the portion of the subject while the second medical imaging system is acquiring the second medical imaging data. This may be beneficial because it may enable the improvement of combined imaging modalities such as PET and magnetic resonance imaging.

In another embodiment the medical instrument further comprises a therapy system configured for depositing energy into a target zone of the subject. The camera system is configured for imaging the portion of the subject when the therapy system is depositing energy into the target zone. This may be beneficial because if the subject is moving in an uncontrolled fashion the targeting of the subject may be less accurate.

In some embodiments the therapy system may be combined with the medical imaging system. For example, the therapy system could be a radiotherapy system, a high intensity ultrasound system, a catheter ablation system or other therapy system. These for example may be combined with magnetic resonance imaging for provide guidance of the targeting of the subject.

In another aspect the invention provides for a computer program product comprising machine-executable instructions for execution by a processor controlling the medical instrument. The medical instrument comprises a camera system for imaging a portion of the subject reposing on a subject support. The medical instrument further comprises a display system for rendering a position feedback indicator. The display system is configured such that the position feedback indicator is visible to the subject when the subject is reposing on the subject support.

Execution of the machine-executable instructions causes the processor to acquire a base position image using the camera system. Execution of the machine-executable instructions further cause the processor to repeatedly acquire a subsequent image using the camera system. Execution of the machine-executable instructions further cause the processor to repeatedly calculate a image transformation from voxels of at least a portion of the base position image to voxels of the subsequent image by inputting the base position image and the subsequent image into an image transformation algorithm. Execution of the machine-executable instructions further causes the processor to repeatedly render a position feedback indicator on the display. The position feedback indicator is controlled by the image transformation.

In another aspect the invention provides for a method of operating a medical instrument. The medical instrument comprises a camera system for imaging a portion of the subject reposing on a subject support. The medical instrument further comprises a display system for rendering a position feedback indicator. The display system is configured such that the position feedback indicator is visible to the subject when the subject is reposing on the subject support.

The method comprises acquiring a base position image using the camera system. The method further comprises repeatedly acquiring a subsequent image using the camera system. The method further comprises repeatedly calculating an image transformation from the voxels of at least a portion of the base position image to voxels of the subsequent image by inputting the base position image and the subsequent image into an image transformation algorithm. The method further comprises repeatedly rendering a position feedback indicator on the display. The position feedback indicator is controlled by the image transformation.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical imaging data is defined herein as two or three-dimensional data that has been acquired using a medical imaging scanner or a medical imaging system. A medical imaging scanner or system is defined herein as an apparatus adapted for acquiring information about the physical structure of a patient and construct sets of two dimensional or three-dimensional medical imaging data. Medical imaging data can be used to construct visualizations which are useful for diagnosis by a physician. This visualization can be performed using a computer.

Magnetic Resonance Imaging (MRI) data is an example of medical imaging data and is defined herein as being the recorded measurements of radio frequency signals emitted by atomic spins using the antenna of a Magnetic resonance apparatus during a magnetic resonance imaging scan. A Magnetic Resonance image or MR image is defined herein as being the reconstructed two or three-dimensional visualization of anatomic data contained within the magnetic resonance imaging data. This visualization can, for example, be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
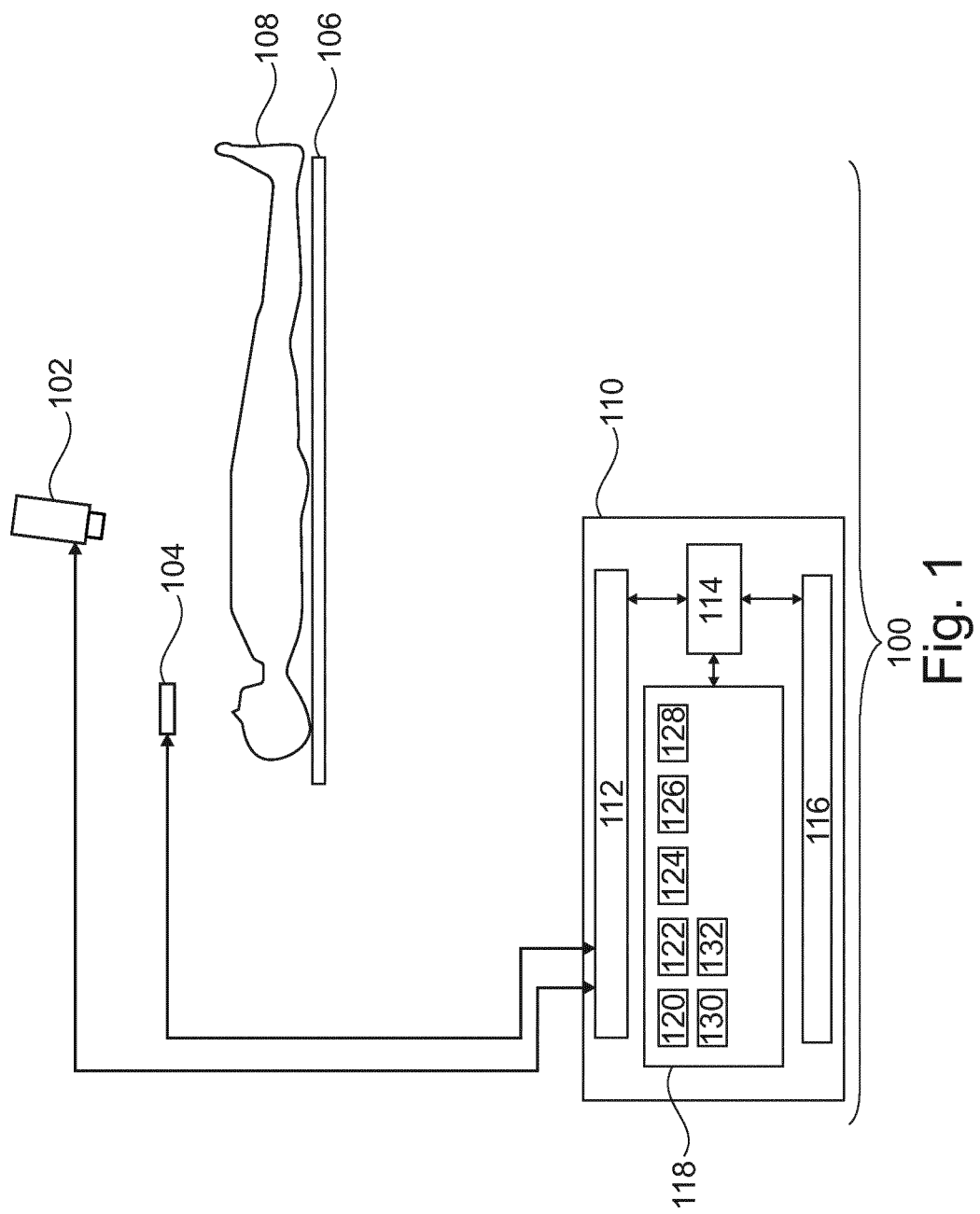
FIG. 1 illustrates an example of a medical instrument.

FIG. 1 illustrates an example of a medical instrument 100. The medical instrument 100 is shown as comprising a camera system 102 and a display system 104. There is a support 106 which is shown as supporting a subject 108. The camera system 102 is configured for imaging a portion of the subject 108. The display 104 is arranged for displaying a position feedback indicator in a visible manner to the subject 108. The camera system 102 and the display system 104 are connected to a hardware interface 112 of a computer system 110. The computer is further shown as comprising a processor 114 that is also in communication with a hardware interface 112, a user interface 116, and a memory 118. The memory 118 may be any combination of memory which is accessible to the processor 114. This may include such things as main memory, cached memory, and also non-volatile memory such as flash RAM, hard drives, or other storage devices. In some examples the memory 134 may be considered to be a non-transitory computer-readable medium.

The memory 118 is shown as containing machine-executable instructions 120 which enable the processor 114 to both control the operation and function of the medical instrument 100 as well as to perform calculations and manipulate data. The memory 118 is further shown as containing a base position image 122 that is acquired with the camera system 102. The memory 118 is further shown as containing a subsequent image 124 that was acquired after the base position image 122. The subsequent image 124 may be acquired repeatedly. For example, the camera system 102 could be a video system which continually provides a video feed.

The memory 118 is further shown as containing an image transformation 126 that was calculated by inputting the base position image 122 and the subsequent image 124 into an image transformation algorithm 128. The image transformation algorithm 128 is shown as being stored in the memory 118 also. The machine-executable instructions 120 then use the image transformation algorithm 128 to generate a rendering 130 of a position feedback indicator. The position feedback indicator is configured for displaying to the subject 108 when the subject is in a different or out of position. The memory 118 is also shown as containing an optional average transformation quantity 132 that was calculated from at least a portion of the image transformation 126. The average transformation quantity 132 may for example be used for simplifying control of the position feedback indicator 130.

Figure 2:
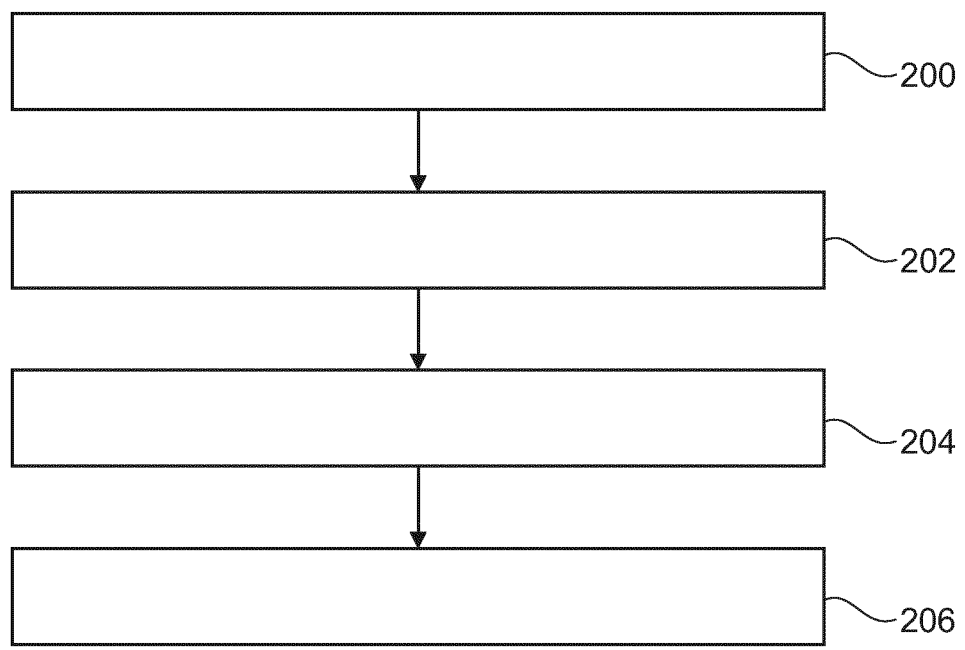
FIG. 2 shows a flow chart which illustrates a method of operating the medical instrument of FIG. 1.

FIG. 2 illustrates an example of a flowchart of a method of controlling the medical instrument 100 of FIG. 1. First in step 200 the processor 114 controls the camera system 102 to acquire the base position image 122. Next in step 202 the processor 114 controls the camera system 102 to repeatedly acquire the subsequent image 124. After a subsequent image 124 has been acquired the method proceeds to step 204 where the processor repeatedly calculates an image transformation 126 from voxels of at least a portion of the base position image 122 to voxels of the subsequent image 124 by inputting the base position image 122 and the subsequent image 124 into an image transformation algorithm 128. Finally, in step 206 the processor 114 repeatedly renders the position feedback indicator 130 and displays this on the display 104. The subject 108 can use the rendering of the position feedback indicator 130 to self-adjust his or her position.

Figure 3:
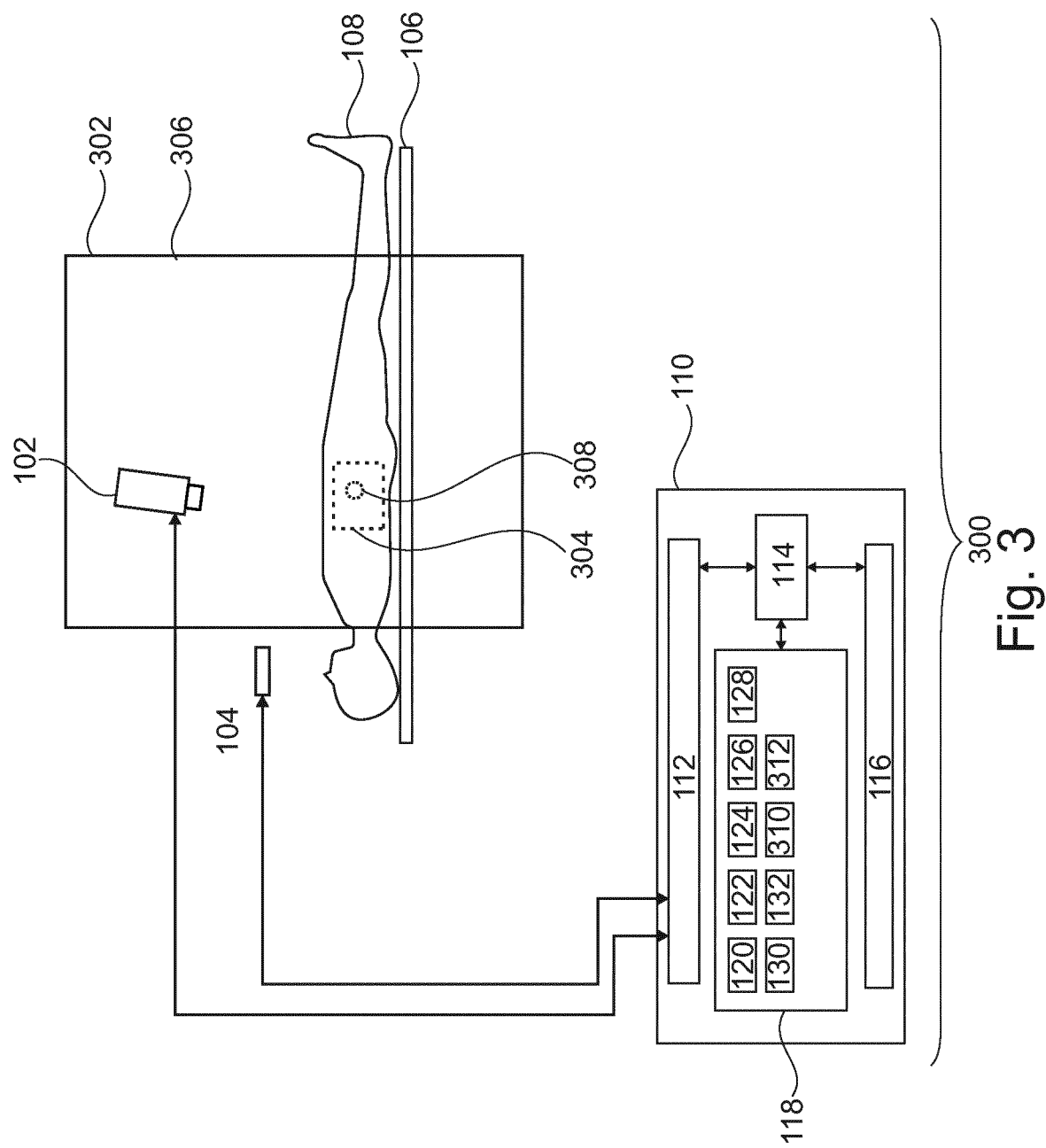
FIG. 3 illustrates a further example of a medical instrument.

FIG. 3 illustrates a further example of a medical instrument 300. The medical instrument illustrated in FIG. 3 is similar to the medical instrument 100 of FIG. 1. In FIG. 3 the medical instrument 300 is further shown as containing one or more medical imaging systems 302 and/or a therapy system 306. The one or more medical imaging systems 302 could for example be a PET system, a CT system, an MRI system, a SPECT system or any one of the two of those. They could for example acquire medical imaging data 310 from an imaging zone 304. In the case where the medical instrument 300 comprises a therapy system 306 the therapy system could direct energy into a target zone 308. The therapy system 306 could for example be a LINAC, an X-ray therapy system, a gamma ray treatment system, a high intensity ultrasound system, or a catheter ablation system. The memory 118 is shown as containing medical imaging data 310 that was acquired using the one or more medical imaging systems 302 and the therapy system control commands 312 that are used to control the targeting of the target zone 308. In instances where there are one or more medical imaging systems 302 and also a therapy system 306, the medical imaging data 310 may for example be useful for reconstructing images which can be used to adjust and thereby control the therapy system 306. For example, medical imaging data could be used to make changes in the therapy system control commands 312. The camera 102 captures motion of the subject 108 and this is able to be displayed on the display system 104. This may help improve the accuracy of any medical imaging or therapy that is performed with the medical instrument 300.

Figure 4:
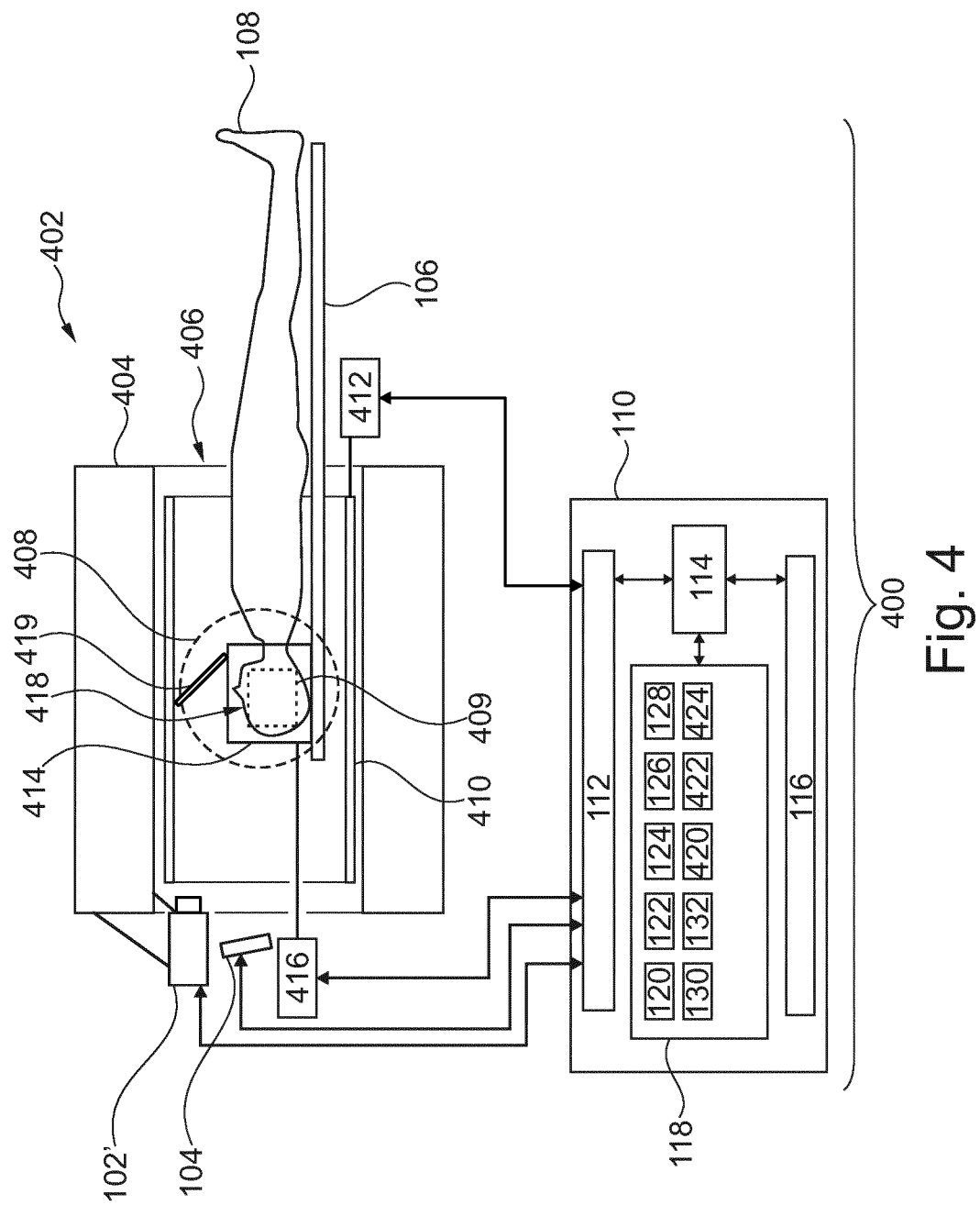
FIG. 4 illustrates a further example of a medical instrument.

FIG. 4 illustrates a further example of the medical instrument 400. In this example the medical instrument 400 is shown as additionally comprising a magnetic resonance imaging system 402. The magnetic resonance imaging system 402 comprises a magnet 404. The magnet 404 is a superconducting cylindrical type magnet with a bore 406 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 406 of the cylindrical magnet 404 there is an imaging zone 408 where the magnetic field is strong and uniform enough to perform magnetic resonance imaging. A region of interest 409 is shown within the imaging zone 408. The magnetic resonance data that is acquired typically acquired for the region of interest. The subject 108 is shown as being supported by the subject support 106 such that at least a portion of the subject 108 is within the imaging zone 408 and the region of interest 409.

Within the bore 406 of the magnet there is also a set of magnetic field gradient coils 410 which is used for acquisition of preliminary magnetic resonance data to spatially encode magnetic spins within the imaging zone 408 of the magnet 404. The magnetic field gradient coils 410 connected to a magnetic field gradient coil power supply 412. The magnetic field gradient coils 410 are intended to be representative. Typically magnetic field gradient coils 410 contain three separate sets of coils for spatially encoding in three orthogonal spatial directions. A magnetic field gradient power supply supplies current to the magnetic field gradient coils. The current supplied to the magnetic field gradient coils 410 is controlled as a function of time and may be ramped or pulsed.

Adjacent to the imaging zone 408 is a head coil 414 for manipulating the orientations of magnetic spins within the imaging zone 108 and for receiving radio transmissions from spins also within the imaging zone 108. A head region of the subject is shown as being within the imaging zone 408. In this example the radio-frequency coil is a head coil 414. The head coil 414 is shown as surrounding the head of the subject 108. There is a region of interest 409 that images a portion of the subject's head region. On a flange of the magnet 404 there is a camera system 102'. The camera 102' may for example be referred to as a flange-mounted camera. The camera 102' looks into the bore 106 of the magnet.

There is a mirror 419 positioned in the bore 406 so that the flange mounted camera 102' is able to image a facial region 418 of the subject 108. The display system 104 is positioned such that the subject 108 can also look into the same mirror 419 and see the rendering of the position feedback indicator 130. That may be beneficial because magnetic resonance imaging protocols may take an extended duration of time and the incorporation of the position feedback indicator 130 may assist the subject 108 in remaining still and/or returning to the same position after moving. The image transformation 126 may also be used to discard portions or reacquire portions of the magnetic resonance imaging data 422. For example, sequentially acquired frames from the camera system 102 may be checked for motion between the images that can be used to validate or invalidate motions which are uncontrollably performed by the subject 108.

A mirror may be provided for imaging the facial region 419 even when there is not a head coil 414. For example, the mirror 419 may be incorporated into a headgear or support which is attached to the subject's head in other examples.

The head coil 414 (or radio frequency coil or antenna) may contain multiple coil elements. The radio frequency antenna may also be referred to as a channel or antenna. The radio-frequency coil 414 is connected to a radio frequency transceiver 416. The radio-frequency coil 414 and radio frequency transceiver 416 may be replaced by separate transmit and receive coils and a separate transmitter and receiver. It is understood that the radio-frequency coil 414 and the radio frequency transceiver 416 are representative. The radio-frequency coil 414 is intended to also represent a dedicated transmit antenna and a dedicated receive antenna. Likewise the transceiver 416 may also represent a separate transmitter and receivers. The radio-frequency coil 414 may also have multiple receive/transmit elements and the radio frequency transceiver 416 may have multiple receive/transmit channels. For example if a parallel imaging technique such as SENSE is performed, the radio-frequency coil 114 will have multiple coil elements.

The computer memory 118 is further shown as containing pulse sequence commands 420. The pulse sequence commands are configured for controlling the magnetic resonance imaging system 402 to acquire magnetic resonance imaging data 422 from the subject 108 according to a magnetic resonance imaging protocol. The memory is further shown as containing a magnetic resonance image 424 that was reconstructed from the magnetic resonance imaging data 422.

Figure 5:
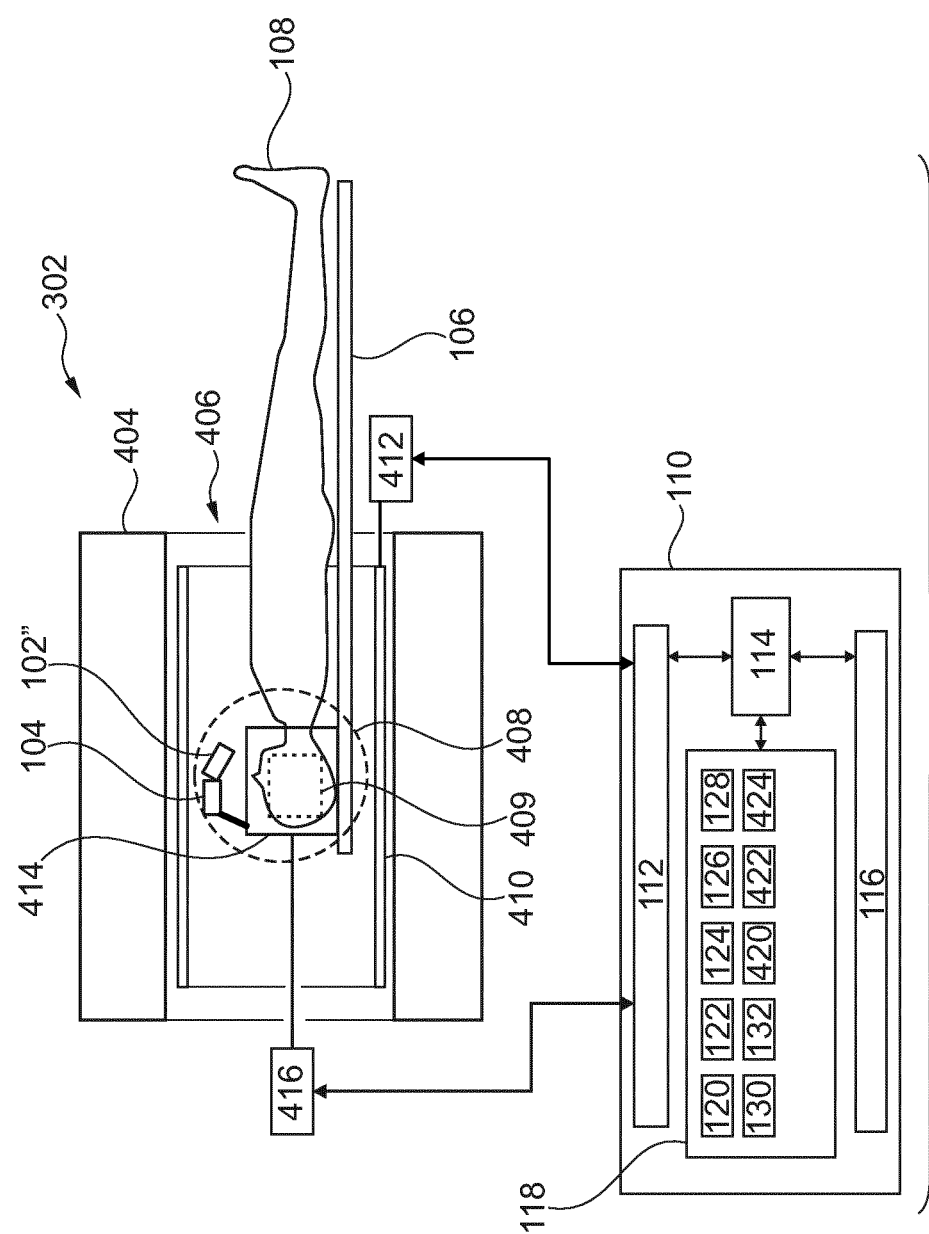
FIG. 5 illustrates a further example of a medical instrument.

FIG. 5 illustrates a further example of a medical instrument 500. The medical instrument 500 in FIG. 5 is similar to the medical instrument 400 in FIG. 4 except in this example the head coil 414 incorporates a camera 102" and a display system 104 that are mounted to and attached to the head coil 414. The data bus for the head coil 414 could for example also be used for the camera 102" and the display system 104. The camera system 102" is configured for imaging a facial region 418 of the subject 108. The display system 104 is configured so that the subject 108 can see the rendering of the position feedback indicator 130.

Figure 6:
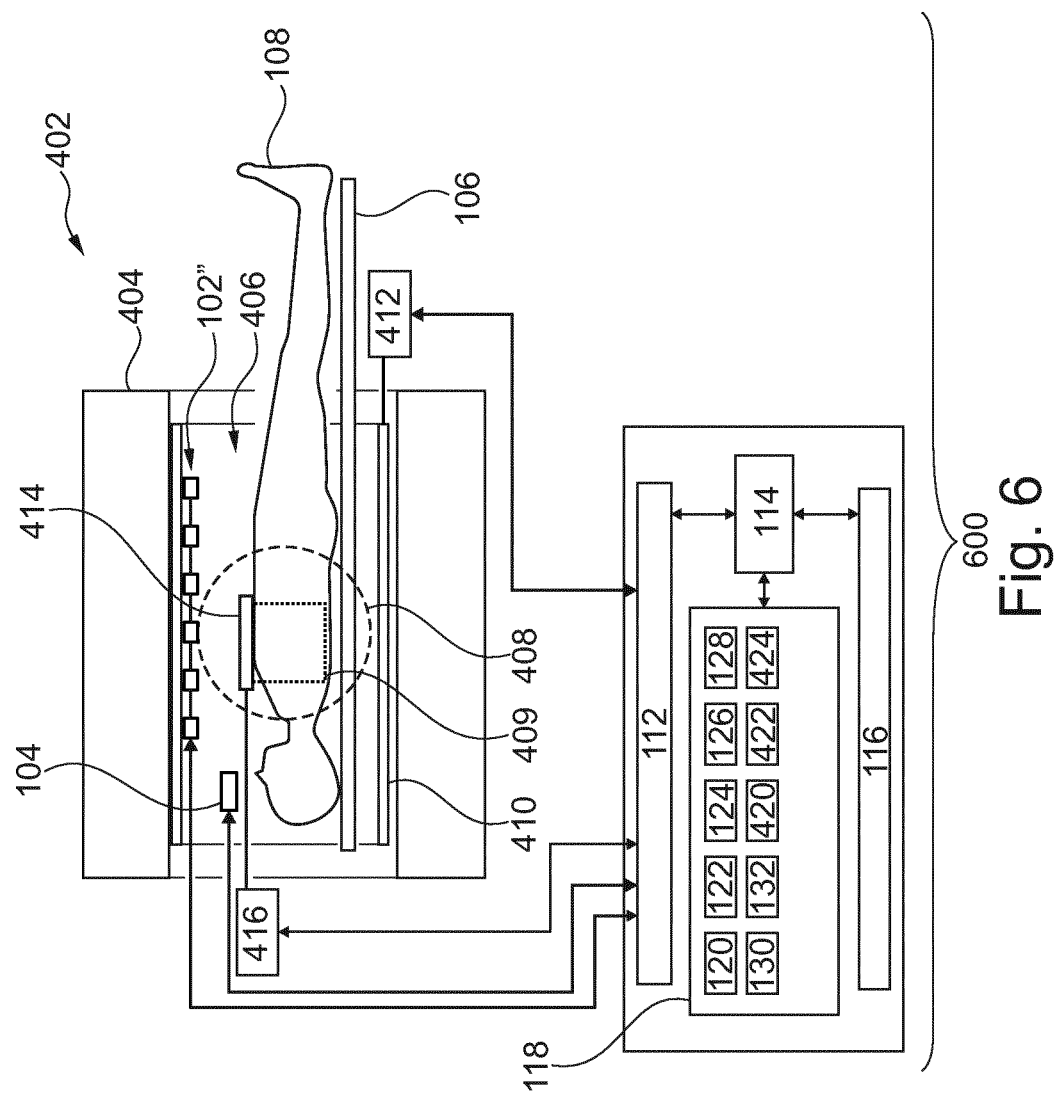
FIG. 6 illustrates a further example of a medical instrument.

FIG. 6 shows a further example of a medical instrument 600 that is similar to the medical instruments 500 in FIGS. 5 and 400 in FIG. 4. In this example the camera system 102 comprises multiple bore mounted cameras 102". The subject 108 can simply be inserted into the bore of the magnet 406 and then any one of the multiple bore mounted cameras 102" can be chosen for generating or acquiring the base position image 122 and any subsequent images 124. There is a radio-frequency coil 414 on the chest of the subject 108 that is connected to the transceiver 416. The display system 104 may for example also be mounted on the bore 406 of the camera or be provided as a camera or other wearable device to position the rendering of the position feedback indicator 130 in a position visible by the eyes of the subject 108.

Figure 7:
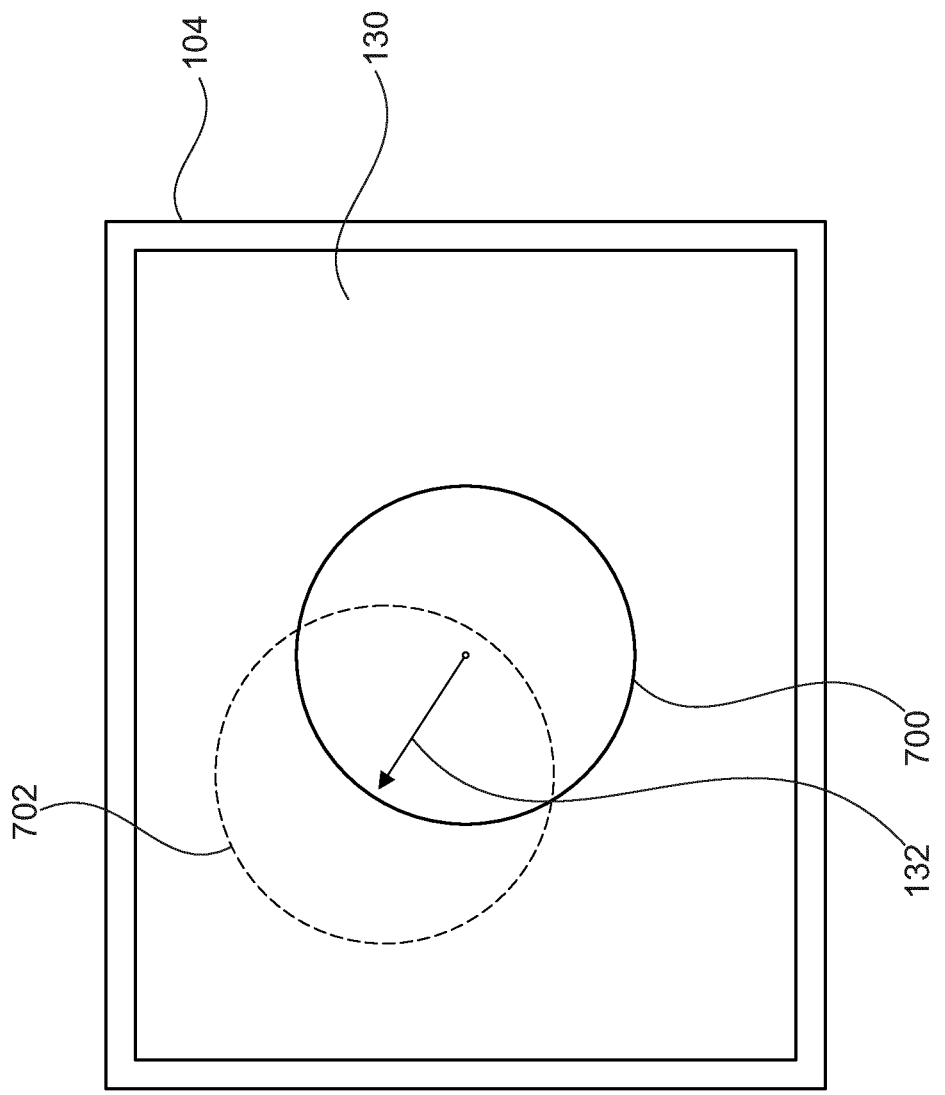
FIG. 7 illustrates an example of a rendering of a position feedback indicator.

FIG. 7 illustrates an example of a display system 104 which is a rendering of the position feedback indicator 130. On this display are two circles 700, 702 visible. The circle 700 represents the initial position of the subject. The circle with the dashed line 702 indicates a current position of the subject. If a region of interest of the image transformation 126 is used to calculate an average transformation quantity 132 such a rendering 130 can be easily calculated. The vector 132 illustrates a vector distance between the circles 700 and 702. The vector 132 may be the average transformation quantity 132 that is calculated from the image transformation 126.

As was mentioned above, motion management is important for many tomographic imaging modalities such as CT or MRI. Triggering and gating mechanisms are widely used to reduce motion artifacts. MRI Navigators can be used to track the motion but they require measurement time. External sensors and cameras can be used to circumvent this but can have limitations as a surrogate of the actual motion to be compensated. In addition, triggering and gating reduces scan efficiency significantly. Prospective gating and triggering is often used however this changes the steady state of the acquisition and can be difficult to apply in some patients. Monotonous scanning also frequently leads to patients falling asleep which can strongly deteriorate compliance.

Examples may use a camera sensor (e.g. camera system 102, 102', 102") to calculate and provide highly sensitive three-dimensional displacement visual feedback (e.g. the position feedback indicator 130) to the subject 108 which it can use to freeze the gross subject or target anatomy pose as much as possible. This is combined with retrospective gating of transient motion like eye blinking, swallowing, coughing, pulse and so forth. By retrospective data validation and invalidation, the steady state and contrast is unchanged for a given sequence. Scan efficiency is high since to a large extent only data where transient motion had occurred has to be invalidated.

In one example a two-dimensional in-bore camera 102" is used for acquiring video data 122, 124 from a relevant part of the patient surface. An additional mirror 419 or other means to guide the visual feedback to the patient's eyes is used. From the camera frames a reference frame is extracted at the start of k-space traversal. Motion displacement is calculated from subsequent frames relative to the reference frame. The motion magnitude field (e.g. vector mapping or image transformation 126) may be displayed as false color image, the patient's task is to make the motion magnitude as low and flat as possible by keeping the target anatomy as close to the reference as possible. The mean magnitude is calculated and transmitted to the scanner for validation/invalidation of the MRI data along with a calculated reasonable threshold for the subject. For additional guidance, the motion vectors are displayed so the patient can revert e.g. eventual accidental head motion. The divergence field of the two-dimensional motion vector field is computed to detect through-plane displacement and the mean divergence is displayed to the patient yielding a sensitive measure for the z-component along the projection direction of the camera. This is possible because the lighting can be fully controlled in a MRI scanning environment and motion to be tracked is very small with minimal variation in the scene, thus vector field divergence can be almost fully contributed to through-plane motion. Overall this results in a very sensitive three-dimensional displacement detector which allows the subject to correct for very tiny motion and thus freeze the pose. Alternatively, more sophisticated three-dimensional sensing technology could be used (three-dimensional ToF, three-dimensional structured light, stereo/multi vision).

Visual feedback (via a position feedback indicator) may have the advantage of actively including the subject in the scanning procedure. Simplified or adapted feedback like Gamification can be used to add an entertainment component or for simplification as needed depending on the subject. It is proposed to have a set of feedback variants to choose to accommodate to the patient's preferences and capabilities.

Instead of only using a static reference image (base position image) acquired at the start of the scan, also frame-to-frame motion can be calculated to detect transient motion events and invalidate respective k-space data. For this mode it is assumed that the subject returns into the original resting state after transient motion has occurred. Typical examples include tremor, coughing, eye blinking, swallowing. It is also possible to switch to this mode or adapt motion thresholds for invalidation on-the-fly during scanning which can be desirable in case the subject is not able follow the visual feedback. This can also be done automatically in case scan efficiency drops too much.

Generally using the image transformation calculation, an estimate or prediction of image quality is possible. This estimate of the image quality may be provided to the operator. The operator may decide what action to take based on the prediction of the image quality. Alternatively, this can be used to adapt algorithm parameters such as invalidation threshold automatically.

Above detection of intermittent short motion events using frame-to-frame displacement measurement can be also used to trigger the acquisition of a short scout scan to measure the new resting state and eventually adapt the acquisition.

Examples may find application for high quality brain imaging, fMRI, pediatric scanning Examples may also be applied to head scanning but also to general breathing motion management, e.g. breathing sensing, breathing type classification and highly precise reproduction of breath-holds. Such precise control of breath-holds or breathing in general is very relevant to avoid morphologic distortion and diagnostic failure/misinterpretation (e.g. hypertrophy in cardiac MRI) or to ensure accurate lesion localization.

Figure 8:
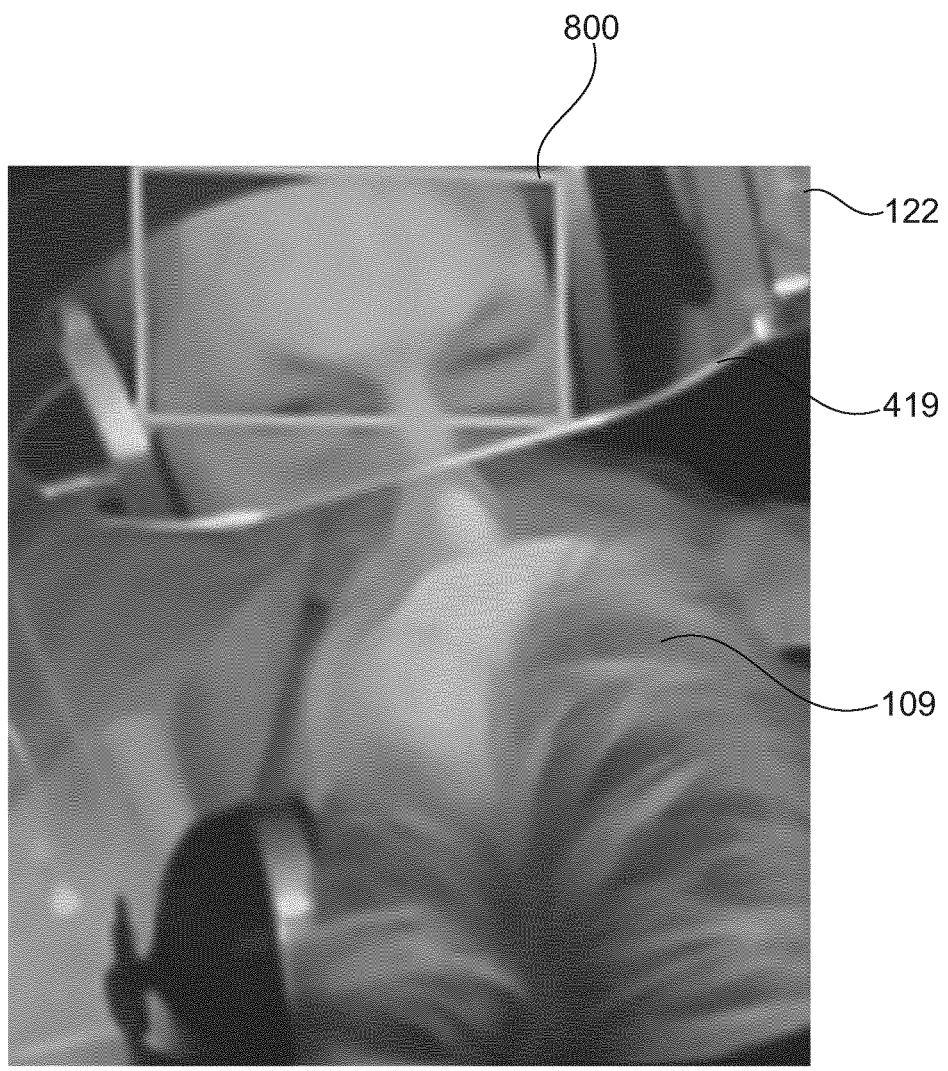
FIG. 8 illustrates an example of a base position image.

FIG. 8 illustrates an example of a base position image 122. A subject 108 is visible in the image. The image was taken from outside the bore of the magnetic resonance imaging system. A mirror 419 visible in the image 122 shows a reflection of the subject 108. There is a region of interest 800 that has been selected to identify motion of the subject.

Figure 9:
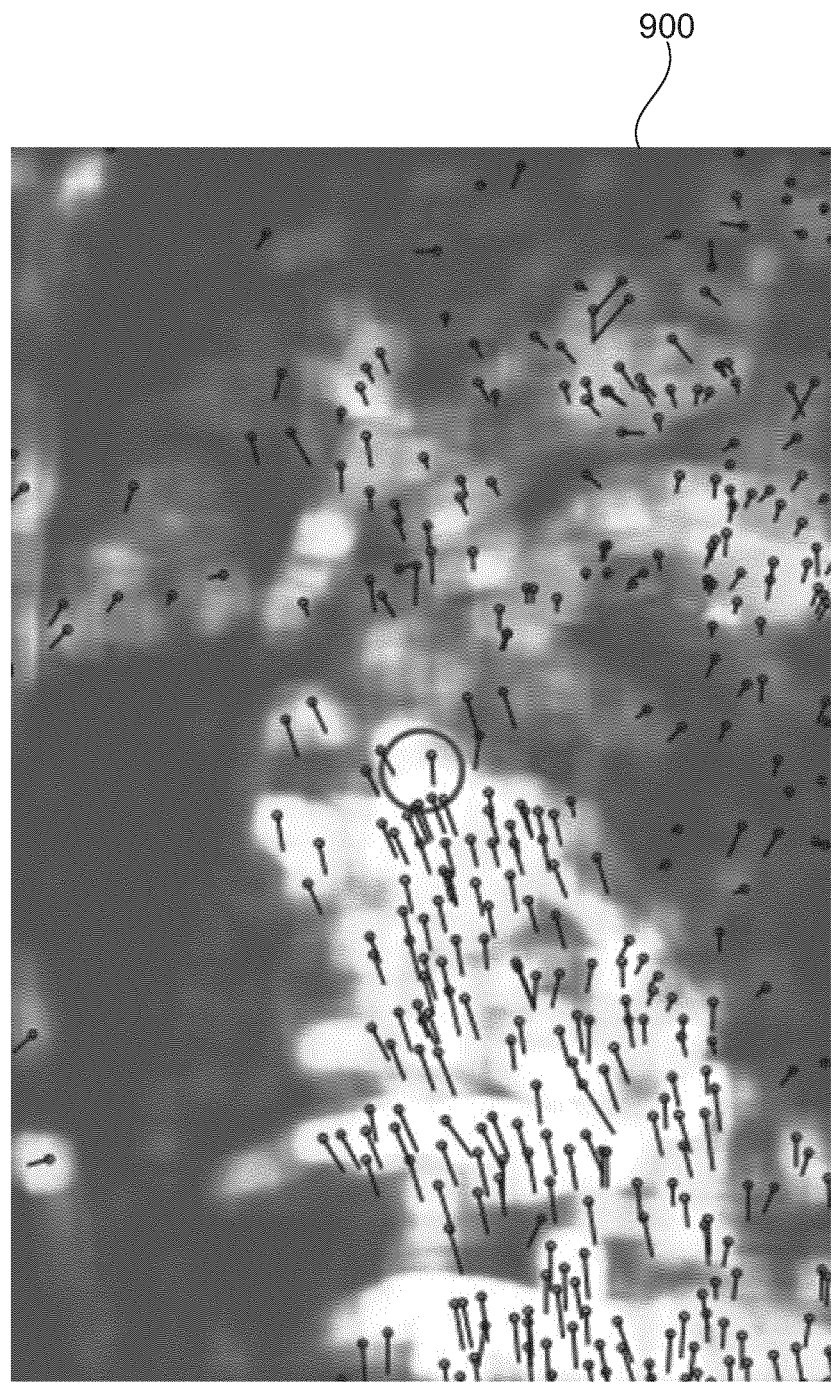
FIG. 9 illustrates a further example of a rendering of a position feedback indicator.

FIG. 9 shows an example of a rendering of the image transformation 900 in this case the image transformation is a vector mapping. The top portion of the rendering 900 is identical with the region of interest 800. This vector mapping 900 has been successfully used as the position feedback indicator for several magnetic resonance imaging experiments. With some practice the subject 108 was able to control and maintain his position during the acquisition of magnetic resonance imaging data.

Figure 10:
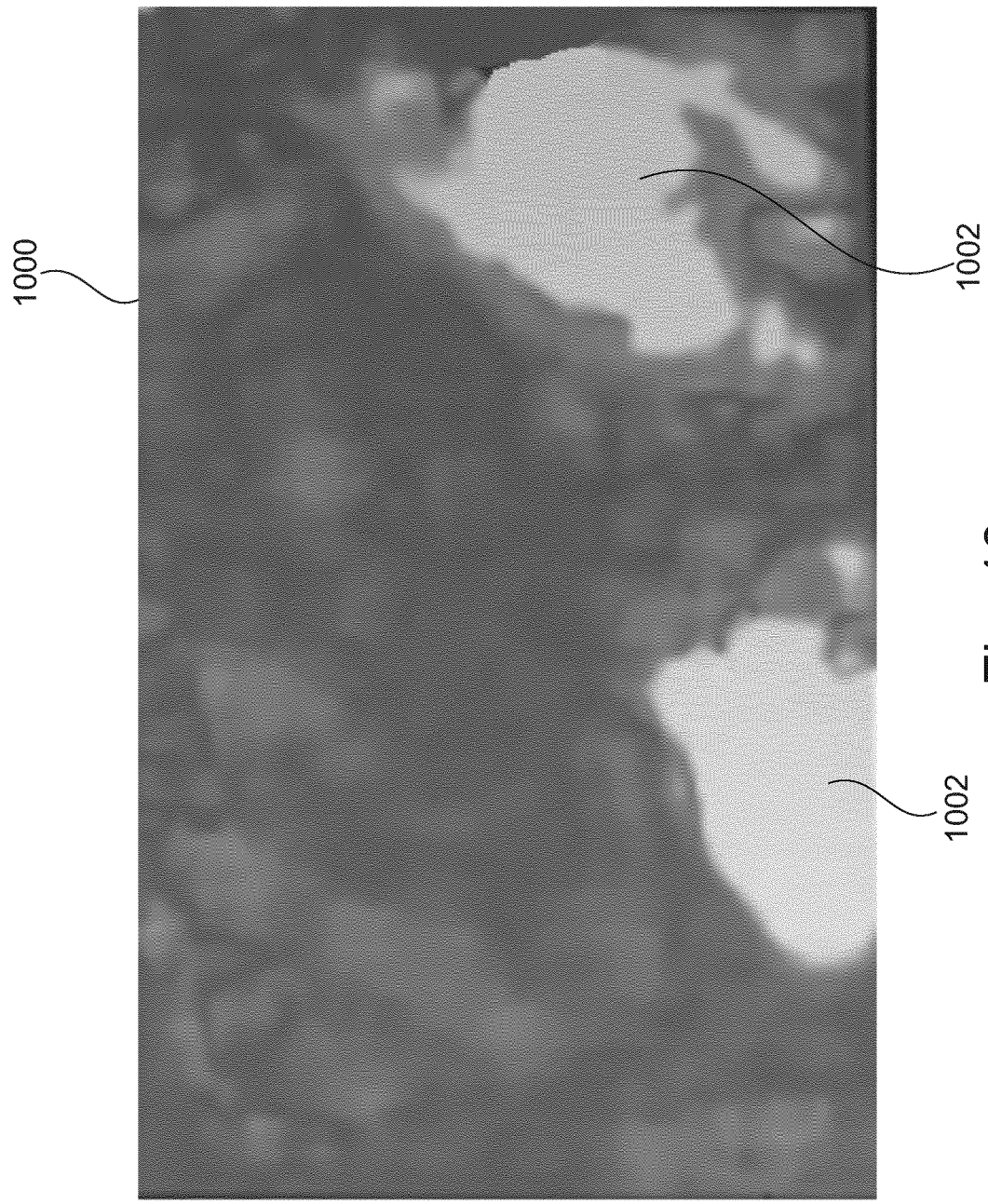
FIG. 10 illustrates a further example of a rendering of a position feedback indicator.

FIG. 10 illustrates another use of the images that were taken subsequent to image 122 in FIG. 8. By comparing adjacent images, a grayscale image was used to indicate the magnitude of motion between subsequent images. The regions labeled 1002 are lighter than the rest of the image and correspond to regions of high motion. These regions 1002 correspond to the position of the eyes and eyelids of the subject 108. The image 1000 may be used to identify when the subject 108 performs involuntary or quick motions which are only temporary. The image 1000 could for example be used to decide which portions of magnetic resonance imaging to discard and which to use during image reconstruction.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical instrument
102 camera system
102' flange mounted camera
102" multiple bore mounted cameras
104 display system
106 support
108 subject
110 computer system
112 hardware interface
114 processor
116 user interface
118 memory
120 machine executable instructions
122 base position image
124 subsequent image
126 image transformation
128 image transformation algorithm
130 rendering of position feedback indicator
132 average transformation quantity
200 acquire a base position image using the camera system
202 repeatedly acquire a subsequent image using the camera system
204 repeatedly calculate a image transformation from voxels of at least a portion of the base position image to voxels of the subsequent image by inputting the base position image and the subsequent image into a image transformation algorithm
206 repeatedly render a position feedback indicator on the display
300 medical instrument
302 one or more medical imaging system
304 imaging zone
306 therapy system
308 target zone
310 medical imaging data
312 therapy system control commands
400 medical instrument
402 magnetic resonance imaging system
404 magnet
406 bore of magnet
408 imaging zone
409 region of interest
410 magnetic field gradient coils
412 magnetic field gradient coil power supply
414 head coil 414' radio-frequency coil
416 transceiver
418 facial region
419 mirror
420 pulse sequence commands
422 magnetic resonance imaging data
424 magnetic resonance image
700 base position
702 current position
800 region of interest
900 rendering of vector mapping
1000 image

The invention claimed is:

1. A medical instrument comprising:
a medical imaging system configured to acquire medical imaging data from a subject reposing on a subject support;
a camera system for imaging a portion of a subject reposing on the subject support when the medical imaging system is acquiring the medical imaging data from the subject reposing on the subject support;
a display for rendering a position feedback indicator, that represents a displacement of the subject relative to an initial position of the subject, wherein the display is configured such that the position feedback indicator is visible to the subject when the subject is reposing on the subject support;
a memory for storing machine executable instructions;
a processor for controlling the medical instrument, wherein execution of the machine executable instructions causes the processor to:
acquire a base position image using the camera system, the base position image corresponding to the initial position of the subject;
acquire a subsequent image using the camera system;
calculate an image transformation from voxels of at least a portion of the base position image to voxels of the subsequent image by mapping a displacement of voxels in the base position image to a location in the subsequent image, wherein the mapping of the displacement of voxels in the base position image to a location in the subsequent image is indicative of a movement change in the initial position of the subject; and
render a position feedback indicator on the display, wherein the position feedback indicator is controlled by the image transformation;
wherein the acquisition of the subsequent image, the calculation of the image transformation, and the rendition of the position feedback indicator are repeated to provide real time feedback to the subject about the displacement of the subject relative to the initial position of the subject while the subject is reposing on the subject support.

2. The medical instrument of claim 1, wherein execution of the machine executable instructions further causes the processor to calculate an average image transformation quantity for voxels with a region of interest of the base position image using the image transformation, wherein the position feedback indicator is controlled using the average image transformation quantity.

3. The medical instrument of claim 2, wherein the position feedback indicator shows a displacement of a ball relative to a circle.

4. The medical instrument of claim 1, wherein the position feedback indicator is a rendering of the image transformation.

5. The medical instrument of claim 1, wherein the medical imaging system is configured to acquire the medical imaging data in portions, wherein execution of the machine executable instructions further cause the processor to:
calculate a statistical measure from the image transformation; and
retrospectively validate or invalidate the portions of the medical imaging data by comparing the statistical measure to predetermined criteria.

6. The medical instrument of claim 1, wherein the medical imaging system is configured to acquire the medical imaging data in portions, wherein execution of the machine executable instructions further cause the processor to:
calculate a frame-to-frame image transformation by mapping the displacement of voxels in the base position image to a location in the subsequent images selected from the acquired subsequent images;
calculate a statistical measure from the frame-to-frame image transformation; and
retrospectively validate or invalidate the portions of the medical imaging data by comparing the statistical measure to predetermined criteria.

7. The medical instrument of claim 5, wherein execution of the machine executable instructions further causes the processor to perform any one of the following:
reacquire invalidated portions of the medical imaging data; and
reconstruct a medical image from the medical imaging data, wherein the reconstruction excludes invalidated portions of the medical imaging data.

8. The medical instrument of claim 5, wherein execution of the machine executable instructions further causes the processor to:
calculate the statistical measure;
calculate a statistical variation of the repeatedly calculated statistical measure; and
adjust the predetermined criteria using the statistical variation.

9. The medical instrument of claim 1, wherein the medical imaging system is a magnetic resonance imaging system.

10. The medical instrument of claim 9, wherein the camera system comprises any one of the following:
a head coil mounted camera,
one or more magnet flange mounted cameras; and
combinations thereof.

11. The medical instrument of claim 1, wherein the medical instrument further comprises a second medical imaging system configured to acquire second medical imaging data from the subject, wherein the camera system is configured to image the portion of the subject when the second medical imaging system is acquiring the second medical imaging data.

12. The medical instrument of claim 1, wherein the medical instrument further comprises a therapy system configured to deposit energy into a target zone of the subject, wherein the camera system is configured to image the portion of the subject when the therapy system is depositing energy the target zone.

13. The medical instrument of claim 2, wherein:
the position feedback indicator comprises a graphical vector depicting the average image transformation quantity.

14. The medical instrument of claim 1, wherein the medical imaging system has a bore, and the medical instrument further comprises:
a mirror positioned in the bore, the camera system arranged to image a reflection in the mirror of the portion of the subject reposing on the subject support in the bore when the medical imaging system is acquiring the medical imaging data from the subject reposing on the subject support in the bore.

15. The medical instrument of claim 14, wherein the display is configured such that the position feedback indicator is visible to the subject in the mirror positioned in the bore when the subject is reposing on the subject support in the bore.

16. A non-transitory-computer readable medium storing machine executable instructions for execution by a processor controlling a medical instrument, wherein the medical instrument comprises a camera system configured to image a portion of a subject reposing on a subject support, wherein the medial instrument further comprise a display for rendering a position feedback indicator that represents a displacement of the subject relative to an initial position of the subject, wherein the display is configured such that the position feedback indicator is visible to the subject when the subject is reposing on the subject support, wherein execution of the machine executable instructions causes the processor to:
(i) acquire a base position image using the camera system, the base position image corresponding to the initial position of the subject;
(ii) acquire a subsequent image using the camera system, the base position image corresponding to the initial position of the subject;
(iii) calculate an image transformation from voxels of at least a portion of the base position image to voxels of the subsequent image by mapping a displacement of voxels in the base position image to a location in the subsequent image, wherein the mapping of the displacement of voxels in the base position image to a location in the subsequent image is indicative of a movement change in the initial position of the subject;
(iv) render a position feedback indicator on the display, wherein the position feedback indicator is controlled by the image transformation; and
(v) repeat the operations (i), (ii), (iii), and (iv) to provide real time feedback to the subject about the displacement of the subject relative to the initial position of the subject while the subject is reposing on the subject support.

17. A method of operating a medical instrument, wherein the medical instrument comprises a medical imaging system configured to image medical imaging data from a subject reposing on a subject support, and a camera system configured to image a portion of a subject when the medical imaging system is acquiring the medical imaging data from the subject reposing on the subject support, wherein the medical instrument further comprises a display for rendering a position feedback indicator, that represents a displacement of the subject relative to an initial position of the subject, wherein the display is configured such that the position feedback indicator is visible to the subject when the subject is reposing on the subject support, wherein the method comprises:
(i) acquiring a base position image using the camera system, the base position image corresponding to the initial position of the subject;
(ii) acquiring a subsequent image using the camera system, the base position image corresponding to the initial position of the subject;
(iii) calculating an image transformation from voxels of at least a portion of the base position image to voxels of the subsequent image by mapping a displacement of voxels in the base position image to a location in the subsequent image;
(iv) rendering a position feedback indicator on the display, wherein the position feedback indicator is controlled by the image transformation and the rendered position feedback indicator comprises at least one of a graphical vector depicting a distance and direction of the image transformation and/or a second circle displaced from a first circle depicting the distance and direction of the image transformation; and
(v) repeating the operations (i), (ii), (iii), and (iv) to provide real time feedback to the subject about the displacement of the subject relative to the initial position of the subject while the subject is reposing on the subject support.

* * * * *